(12) United States Patent
Osawa et al.

(10) Patent No.: US 8,159,659 B2
(45) Date of Patent: Apr. 17, 2012

(54) OPTICAL DEVICE INSPECTING APPARATUS

(75) Inventors: Shigemi Osawa, Koushi (JP); Kazuma Komuro, Kumamoto (JP)

(73) Assignee: Japan Electronic Materials Corp., Hyogo (JP)

( * ) Notice: Subject to any disclaimer, the term of this patent is extended or adjusted under 35 U.S.C. 154(b) by 129 days.

(21) Appl. No.: 12/515,213

(22) PCT Filed: Nov. 9, 2007

(86) PCT No.: PCT/JP2007/071846
§ 371 (c)(1),
(2), (4) Date: May 15, 2009

(87) PCT Pub. No.: WO2008/059767
PCT Pub. Date: May 22, 2008

(65) Prior Publication Data
US 2010/0053601 A1    Mar. 4, 2010

(30) Foreign Application Priority Data

Nov. 15, 2006  (JP) .................................. 2006-309472
May 30, 2007  (JP) .................................. 2007-143617

(51) Int. Cl.
*G01B 9/00* (2006.01)
(52) U.S. Cl. ..................................................... 356/124
(58) Field of Classification Search ........... 356/124–128
See application file for complete search history.

(56) References Cited

U.S. PATENT DOCUMENTS

2007/0268483 A1* 11/2007 Yatsugake et al. ......... 356/237.1
* cited by examiner

*Primary Examiner* — Michael P Stafira
(74) *Attorney, Agent, or Firm* — Michael L. Greenberg, Esq.; Greenberg & Lieberman, LLC

(57) ABSTRACT

[PROBLEMS] To provide an optical device inspecting apparatus which can be set to take many objects at one time more freely compared with conventional apparatuses, and furthermore, can accurately inspect even an optical device wherein an optical sensor is offset from a microlens. [MEANS FOR SOLVING PROBLEMS] Provided is an optical device inspecting apparatus having a probe card unit and a lens unit. The probe card unit is provided with a main substrate, a guide plate and a probe. Openings are made on the main substrate and the guide plate. The guide plate is fixed at a prescribed position from the main substrate, and is provided with a plurality of probe inserting holes. The probe is inserted into the probe inserting hole on the guide plate and fixed. The leading end portion of the probe protruding from the inserting hole has a shape of a cantilever. The lens unit using a pupil lens is arranged at the opening on the main substrate, and makes light applied to an inspecting object incline as the light goes further from the center of the optical system.

7 Claims, 5 Drawing Sheets

FIG. 1 (a)
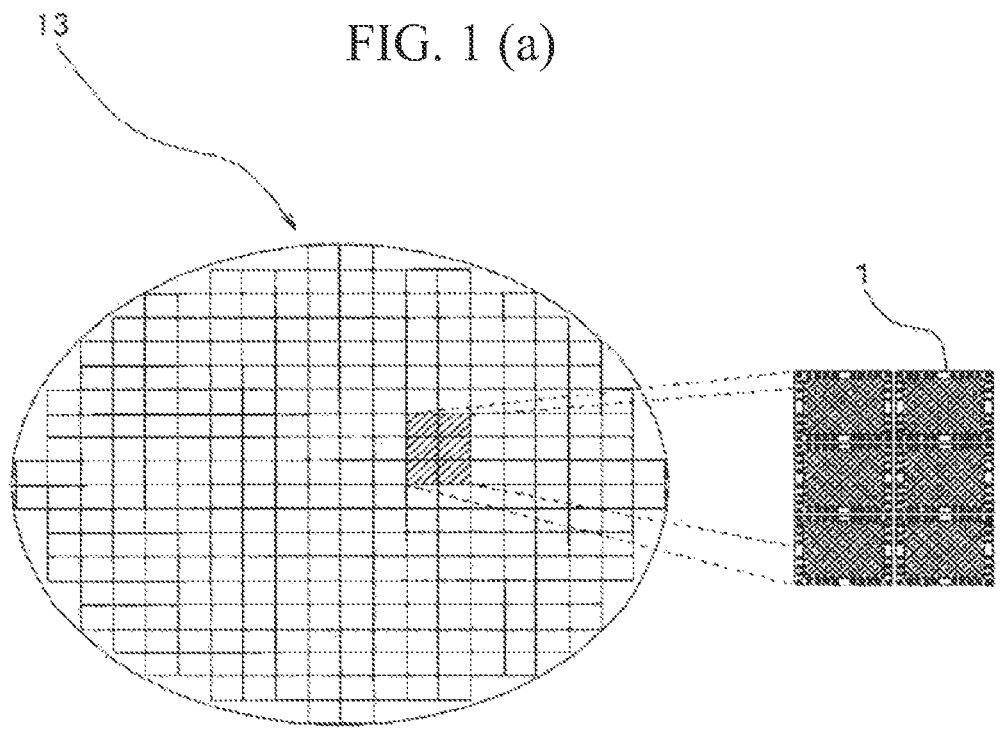
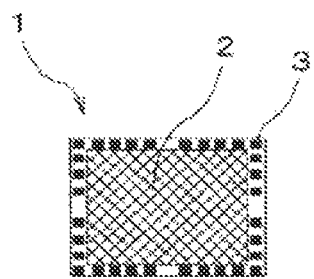
FIG. 1 (b)

OPTICAL DEVICE INSPECTING APPARATUS

TECHNICAL FIELD

The present invention relates to inspection devices for optical devices that are used to inspect so-called optical devices such as photoelectric conversion devices including an image sensor and a solid-state image sensor.

PRIOR ART

Inspection of so-called optical devices such as photoelectric conversion devices including an image sensor and a solid-state image sensor requires measurement of characteristics by projecting light onto an image-sensor member. For example, the inspection of a solid-state image sensor is performed as follows:

A chip of solid-state image sensor 1 has a side length of ten mm or less and is provided with a sensing area 2 in the middle of the chip surface. The sensing area 2 is embedded with hundreds of thousands to millions of optical sensors, and formed along the four sides of the sensing area 2 is an electrode pad 3 (refer to FIG. 1).

To inspect the operation of the solid-state image sensor 1, light is projected onto the sensing area 2, and an electrical characteristic caused by the incident light is evaluated by measuring electrical signals extracted from the electrode pad 3.

Such inspection devices include a device comprising a cantilever-type probe card that includes a lens unit mounted thereto. Japanese Unexamined Patent Application Publication No. 11-26521 discloses an example of such a conventional inspection device.

Japanese Unexamined Patent Application Publication No. 11-26521 discloses an inspection device 18 and an optical device 17 that are integrated. The inspection device 18 is a probe card 16 having, in its center, an opening for projecting light and comprises a cantilever-type probe 15 (refer to FIG. 6).

In designing a probe card comprising the conventional cantilever-type probe used in the above-described inspection device, its structure makes it impossible to arrange the inspection area to be close to the inspection device, and therefore, respective probe-supporting members must be separately provided on a substrate.

In addition, one-by-one measurement of devices on the wafer results in a lengthy inspection time, and therefore, probe cards are required to measure a plurality of devices at a time. To deal with the requirement, a probe card comprising the vertical-type probe is proposed.

Here, the optical device comprises a microlens and an optical sensor. In the case of a solid-state image sensor of one cm square, hundreds of thousands to millions of optical sensors are embedded. Microlenses are provided corresponding to the optical sensors in order to project light onto the optical sensor more effectively.

In the case of an imaging camera using such an optical device, there exists an exit pupil determined by the aperture of the lens. The farther the exit pupil from the center of the optical system, the lower the angle of incident that light will make with the optical sensor. Therefore, corresponding to the angle, the optical sensor is offset outwardly from the microlens as the exit pupil becomes farther from the center.
(Patent Document) Japanese Published Unexamined Patent Application No. H11-26521

SUMMARY OF INVENTION

Problems to Be Solved by the Invention

In inspecting the output sensitivity of the sensor of an optical device whose optical sensor is offset from the microlens as described above, it is problematic that if a collimated beam is used for the inspection, the output sensitivity of a sensor that is offset from the device, especially of a sensor that is greatly offset, represents low, and therefore, even a device of a good quality is determined to be defective.

To deal with the problem of the needle shade cast on projected light which affecting the measurement in taking a plurality of chips, and the problem of projected light affecting adjacent chips because of a projection area 21 being circle while the sensing area 2 is square as illustrated in FIG. 7, the conventional devices take a plurality of chips in diagonal direction and comprise a light reflection plate for projected light.

There are problems, however, with the conventions devices in that some eight chips are the maximum of the number of chips to be taken and in that enlarging the opening to take a plurality of chips causes warp of the substrate and slippage of the needle.

One object of the present invention is to provide an inspection device for an optical device allowing for taking a plurality of chips more freely than the conventional devices and enabling accurate inspection of optical devices whose optical sensor is offset from the microlens.

Means for Solving the Problems

According to the present invention, an inspection device for an optical device including a plurality of optical sensors in a sensing area comprises a light source for projecting light onto the optical device for inspection; wherein a pupil lens is provided between the light source and the sensing area, the pupil lens making the angle of incident of projected light lower as the pupil lens becomes farther from the center of the optical system.

According to the present invention, an inspection device for an optical device comprises: a probe card unit and a lens unit; wherein the probe card unit includes a main substrate, a guide plate and a probe; the main substrate and the guide plate being provided with an opening; the guide plate being fixed to a certain location of the main substrate and provided with a plurality of probe insertion holes; the probe being disposed and fixed in the probe insertion hole of the guide plate, and having a end part projecting out from the insertion hole in the shape of a cantilever; the lens unit including a pupil lens, being disposed in the opening provided in the main substrate, and making the angle of incident of light that is projected onto an device being inspected lower as the pupil lens becomes farther from the center of the optical system.

Preferably, the guide plate is provided with a groove, the probe insertion hole is disposed in the bottom of the groove, and the probe is fixed in the groove with resin.

Preferably, the inspection device further comprises a light blocking member for blocking a beam of light projected by the lens unit onto the probe.

Preferably, the light blocking member is the guide plate.

Advantageous Effects of the Invention

According to the present invention, an inspection device for an optical device including a plurality of optical sensors in a sensing area comprises a light source for projecting light onto the optical device for inspection; wherein a pupil lens is provided between the light source and the sensing area, the pupil lens making the angle of incident of projected light lower as the pupil lens becomes farther from the center of the optical system thereby allowing for inspection of the optical device under the conditions of the actual use.

According to the present invention, an inspection device for an optical device comprises: a probe card unit and a lens unit; wherein the probe card unit includes a main substrate, a guide plate and a probe; the main substrate and the guide plate being provided with an opening; the guide plate being fixed to a certain location of the main substrate and provided with a plurality of probe insertion holes; the probe being disposed and fixed in the probe insertion hole of the guide plate and having a end part projecting out from the insertion hole in the shape of a cantilever; the lens unit including a pupil lens, being disposed in the opening provided in the main substrate, and making the angle of incident of light that is projected onto an device being inspected lower as the pupil lens becomes farther from the center of the optical system thereby enabling inspection of the optical device under the conditions of actual use, which results in a more accurate inspection.

In addition, the guide plate is provided with a groove, the probe insertion hole is disposed in the bottom of the groove, and the probe is fixed in the groove with resin thereby improving the workability in fixing the probe.

Further, the inspection device further comprises a light blocking member for blocking a beam of light projected by the lens unit onto the probe thereby eliminating the harmful effects to adjacent chips.

Further, the light blocking member is the guide plate thereby eliminating the need of an extra light reflection plate.

BRIEF DESCRIPTION OF DRAWINGS

FIG. 1(a) is a plan view of an entire solid-state image sensor that is an optical device and its enlarged partial plan view, and FIG. 1 (b) is a plan view of one of solid-state image sensors extracted;

BEST MODE FOR CARRYING OUT THE INVENTION

Figure 2:
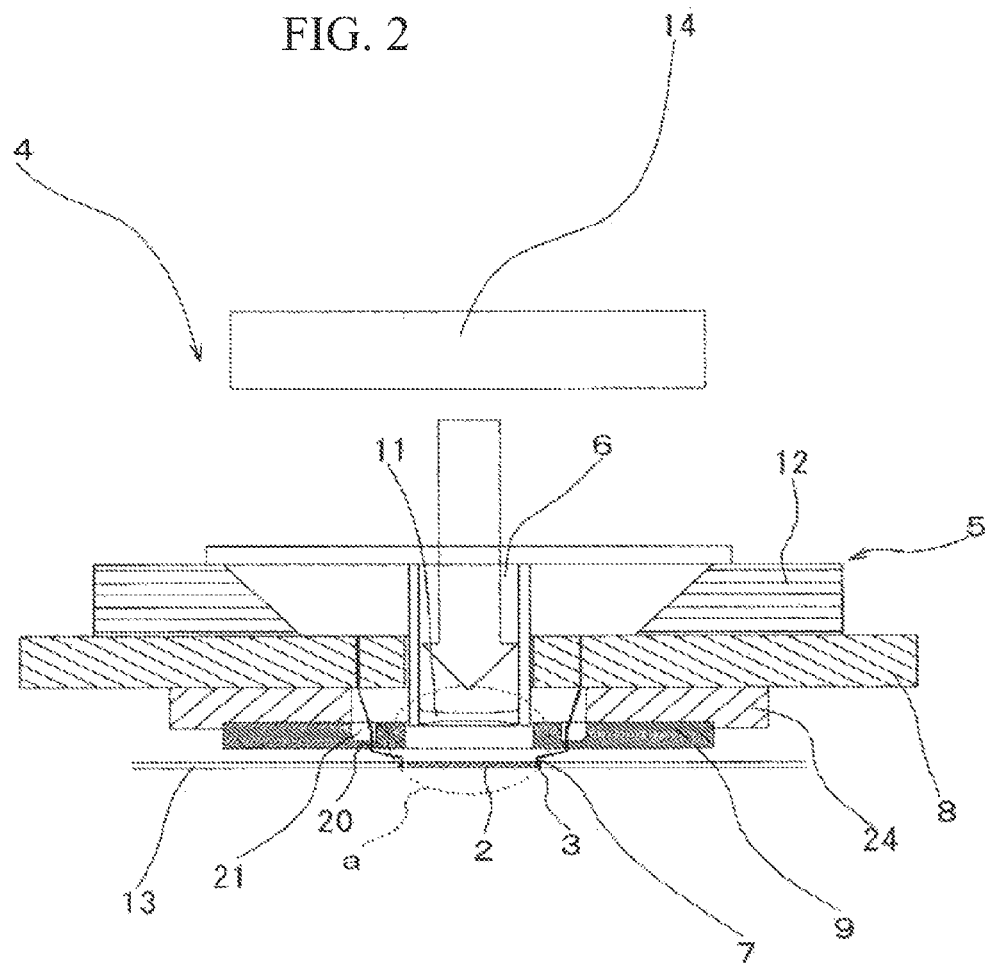
FIG. 2 is a schematic cross sectional view of an inspection device for an optical device.
Figure 3:
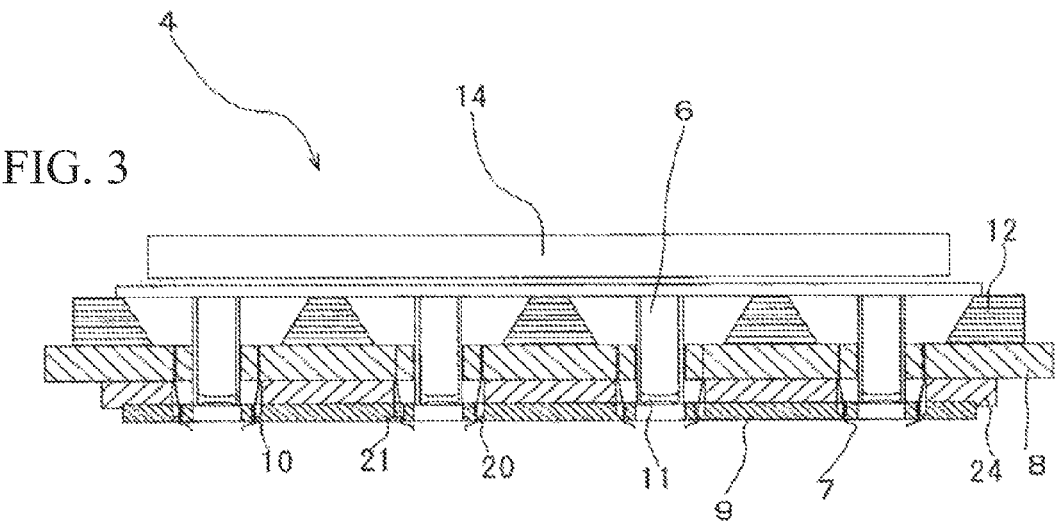
FIG. 3 is a cross sectional view of the entire inspection device for an optical device.

The present invention will now be described more specifically with reference to the drawings. FIG. 2 is a schematic view of an inspection device for an optical device according to the present invention. FIG. 3 is a cross sectional view of the entire inspection device for an optical device.

An inspection device 4 for an optical device according to the present invention comprises a probe card unit 5 and a lens unit 6. The probe card unit 5 and the lens unit 6 are integrated.

The probe card unit 5 comprises a main substrate 8, a guide plate 9 and a probe 7. The main substrate 8 and the guide plate 9 are provided with an opening. The guide plate 9 is fixed to a certain location of the main substrate 8 and provided with a plurality of probe insertion holes 10.

Figure 5:
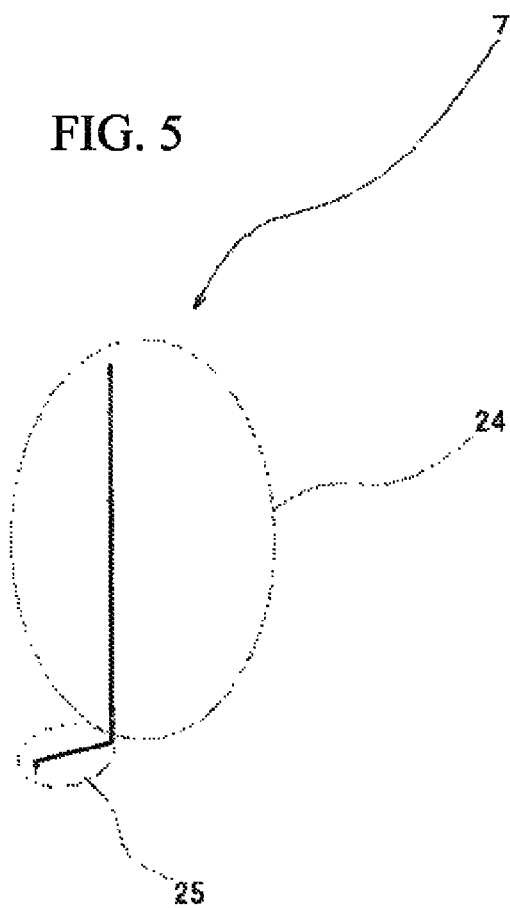
FIG. 5 is an overall view of a probe.
Figure 6:
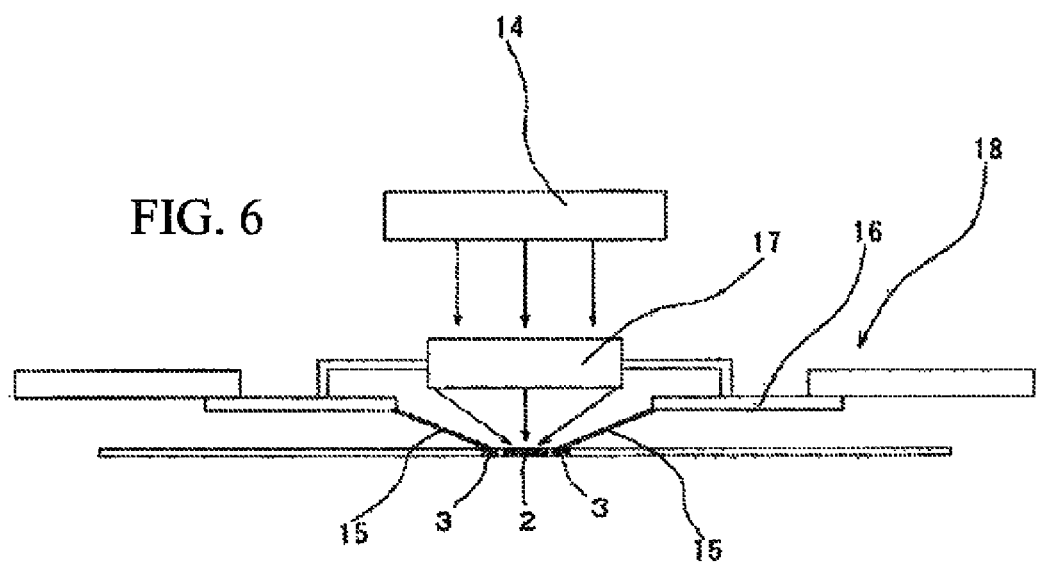
FIG. 6 is a schematic cross sectional view of the conventional inspection device for an optical device.
Figure 7:
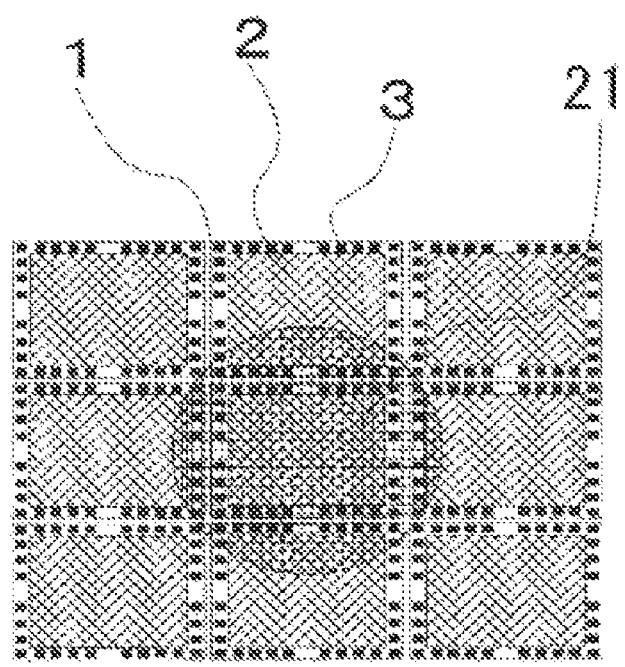
FIG. 7 is a plan view of the projection area given by the conventional inspection device for an optical device.

An insertion part 22 of the probe 7 is disposed and fixed in the probe insertion hole 10 provided in the guide plate 9. An end part 23 of the probe 7 projects out from the probe insertion holes 10. Here, as illustrated in FIG. 5, while the insertion part 22 of the probe 7 is in the shape of a vertical-type probe, the end part 23 is in the shape of a cantilever as the end part 23 bends at a point a little out from the guide plate 9 and extends towards the opening in the guide plate 9. The end of the probe 7 is the needle tip. As described here, the probe 7 according to the present invention takes the shape of both a vertical-type probe and a cantilever-type probe.

The end part 23 of the probe 7 is short enough to be hidden beneath the guide plate 9 thereby solving the problem of light reflected from the probe.

The probe insertion hole 10 is disposed in the bottom of a groove 20 provided in the guide plate 9. The probe 7 is fixed in the groove 20 with resin 21. The probe 7 is fixed with resin with its insertion part 22 projecting a little out from the probe insertion hole 10 in the guide plate 9. Especially, it is preferred that the projecting part of the insertion part 22 be fixed with resin up to the point where the end part 23 starts to bend thereby achieving a high needle pressure.

Here, the cantilever-type probe is a probe that takes, from the part mounted to a substrate to the needle tip, the shape of a cantilever. The cantilever-type probe is fixed to a substrate or the like by connection means such as soldering, and its cantilever shape allows it to change the shape in the lengthwise direction in response to external force. On the other hand, the vertical-type probe is a probe that is in the shape of a substantially straight line. The vertical-type probe is mounted perpendicularly to a substrate by means of a guide plate or the like, and an elastic part provided allows it to change the shape in the lengthwise direction in response to external force. The probe 7 according to the present invention is characterized in that it takes the shape of both types of probes.

The probe 7 is disposed in a through hole provided in the main substrate 8. The probe 7 is fixed to the upper end of the through hole with solder and electrically connected to a trace on the main substrate 8 inside the through hole.

The pitch of each through hole in the main substrate 8 is greater than that of each probe insertion hole 10 in the guide plate 9, and therefore, the insertion part 22 of the probe 7 is a little bent as illustrated in the drawing. The probe 7, for example, is formed of rhenium tungsten, has a diameter of 80 μm, and is disposed at a pitch of 120 μm.

The guide plate 9 is fixed to a certain location of the main substrate 8 with a spacer 24 interposed therebetween. The spacer 24 is a unit holder and formed of stainless-steel or ironic metal. The guide plate 9 is ceramic.

The present embodiment employs a reinforce panel 12 to reinforce the main substrate 8. The reinforce panel is formed of stainless-steel or ironic metal.

The lens unit 6 comprises a pupil lens 11. As the light source, a collimated beam generating less heat such as a LED is used. The pupil lens 11 employed here solves the problems with the conventional inspection devices for an optical device, which determine an optical device of a good quality as defective due to the sensor output sensitivity, which represents low because of the collimated beam used, of the optical device whose optical sensor is greatly offset from the microlens.

More specifically, by using the pupil lens 11 that is the same exit pupil as that used in an imaging camera comprising an optical device, recreated is incident light whose angle with the optical device of the imaging camera becomes lower as the exit pupil becomes farther from the center of the optical system thereby allowing for inspection under the same conditions in which the optical device is actually used. Accordingly, by projecting light properly onto the optical sensor, the problems that arise in inspecting the sensor output sensitivity of an optical device whose optical sensor is offset from the microlens is solved, which allows for more accurate inspection as a device of good quality is no longer determined as defective.

How to inspect an optical device by the inspection device 4 for an optical device according to the present invention will now be explained. In the present embodiment, the solid-state image sensor 1 that is an optical device illustrated in FIG. 1 is inspected at ambient temperature to 60° C.

Figure 4:
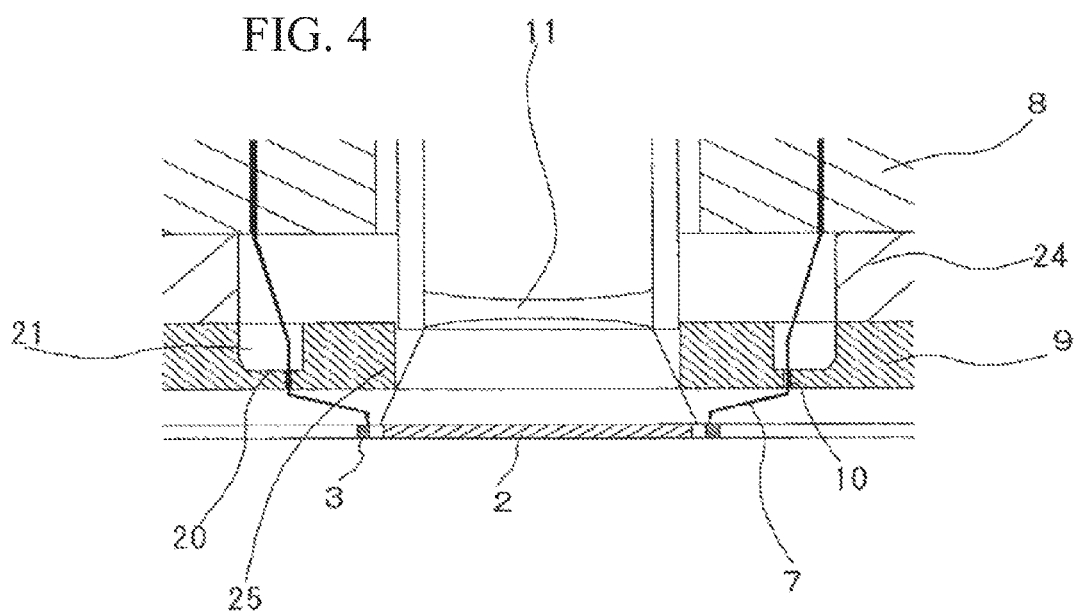
FIG. 4 is an enlarged view of part a illustrated in FIG. 2.

As illustrated in FIG. 4, light from a light source 14 is diffused through the pupil lens 11 of the lens unit 6 and projected onto the optical device that is being measured. At this time, the light passed through the lens unit 6 passes through the opening provided for the guide plate 9. The light projection area is, however, substantially the same as the sensing area 2 of the solid-state image sensor 1 because part of the light is blocked by the guide plate 9, and therefore, adjacent solid-state image sensors 1 are little affected.

As described above, the probe 7 makes contact with the electrode pad 3 with light projected onto the sensing area 2, which allows for measurement of electrical signals extracted from the electrode pad 3 thereby performing inspection of the solid-state image sensor 1.

As described above, instead of a light reflection plate or the like that the conventional inspection devices require, the inspection device 4 for an optical device according to the present invention comprises the guide plate 9 part of which blocks a beam of light as a light blocking member thereby enabling restriction of the projection area.

The inspection device 4 for an optical device according to the present invention comprises, as one unit, a plurality of devices, the structure of which is illustrated in FIG. 2, arranged in a straight line. The unit is mounted to a substrate with a holder. In addition, in arranging the above-mentioned unit, the surface of the unit is made even by means of the unit holder, and the balance of the entire unit is managed by adjusting the balance of the unit with respect to the main substrate.

As described above, the inspection device for an optical device according to the present invention comprises a lens unit including a pupil lens thereby enabling inspection of an optical device under the conditions of actual use, which results in a more accurate inspection.

Further, the inspection device for an optical device according to the present invention comprises a probe that takes the shape of both of the vertical-type probe and the cantilever-type probe thereby overcoming outstanding problems with each type of probe and making use of advantages of each type of probe, which allows the measurement area to be set at will.

Different from the conventional inspection devices, the inspection device for an optical device according to the present invention comprises a probe card unit including a lens unit integrated thereto, instead of being merely combined with, which alleviates limitations on designing held by each part of the conventional devices and allows for an inspection device with improved accuracy.

EXPLANATION OF REFERENCE NUMERALS

1: Solid-State Image Sensor; 2: Sensing Area; 3: Electrode Pad; 4: Inspection Device for Optical Device; 5: Probe Card Unit; 6: Lens Unit; 7: Probe; 8: Main Substrate; 9: Guide Plate; 10: Probe Insertion Hole; 11: Pupil Lens; 12: Reinforce Panel; 13: Wafer; 14: Light Source; 15: Cantilever-Type Probe; 16: Probe Card; 17: Optical Device; 18: Inspection Device; 20: Groove; 21: Resin; 22: Insertion Part; 23: End Part; and 24: Spacer.

The invention claimed is:

1. An inspection device for an optical device, the inspection device comprising:
   a probe card unit; and
   a lens unit;
   wherein the probe card unit includes a main substrate, a guide plate and a probe;
   the main substrate and the guide plate being provided with an opening;
   the guide plate being fixed to a certain location of the main substrate and provided with a plurality of probe insertion holes disposed vertically;
   the probe including an insertion part inserted and fixed in the probe insertion hole and an end part projecting out from the probe insertion hole, the insertion part having a shape of a vertical-type probe, the end part having a shape of a cantilever-type probe, and the end part having a shape of a cantilever-type probe which bends from the end part at a part projecting out from the guide plate to extend towards the opening in the guide plate;
   the lens unit including a pupil lens, being disposed in the opening provided in the main substrate, and making the angle of incident of light that is projected onto an device being inspected lower as the pupil lens becomes farther from the center of the optical system.

2. The inspection device according to claim 1, wherein the guide plate is provided with a groove, the probe insertion hole is disposed in the bottom of the groove, and the probe is fixed in the groove with resin.

3. The inspection device according to claim 1, further comprising a light blocking member for blocking a beam of light projected by the lens unit onto the probe.

4. The inspection device according to claim 3, wherein the light blocking member is the guide plate.

5. The inspection device according to claim 2, further comprising a light blocking member for blocking a beam of light projected by the lens unit onto the probe.

6. The inspection device according to claim 5, wherein the light blocking member is the guide plate.

7. A probe unit comprising:
   a main substrate;
   a guide plate; and
   a probe;
   wherein the guide plate is fixed to a certain location of the main substrate and provided with a plurality of probe insertion holes disposed vertically; and
   the probe having an insertion part inserted and fixed in the probe insertion hole and at an end part projecting out from the plurality of probe insertion holes;
   the insertion part having a shape of a vertical-type probe;
   the end part having a shape of a cantilever-type probe and the end part having a shape of a cantilever-type probe which bends from the end part at a part projecting out from the guide plate to extend towards the opening in the guide plate.

* * * * *